(12) United States Patent
Chambers et al.

(10) Patent No.: US 8,663,320 B2
(45) Date of Patent: Mar. 4, 2014

(54) STORAGE AND LOADING SYSTEM FOR IMPLANTABLE MEDICAL DEVICES

(75) Inventors: Sean D. Chambers, Bloomington, IN (US); Ram H. Paul, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1489 days.

(21) Appl. No.: 12/328,273

(22) Filed: Dec. 4, 2008

(65) Prior Publication Data

US 2009/0143852 A1   Jun. 4, 2009

Related U.S. Application Data

(60) Provisional application No. 61/005,351, filed on Dec. 4, 2007.

(51) Int. Cl.
*A61F 2/24* (2006.01)
*A61F 2/06* (2013.01)

(52) U.S. Cl.
USPC .......................................... 623/2.11; 623/1.1

(58) Field of Classification Search
USPC .............. 606/198; 623/1.11, 1.12, 1.15, 1.24, 623/1.23
See application file for complete search history.

(56) References Cited

U.S. PATENT DOCUMENTS

| | | | |
|---|---|---|---|
| 5,486,193 A | 1/1996 | Bourne | |
| 5,725,519 A | 3/1998 | Penner | |
| 5,928,258 A | 7/1999 | Kahn | |
| 6,090,035 A | 7/2000 | Campbell | |
| 6,096,027 A | 8/2000 | Layne | |
| 6,149,680 A | 11/2000 | Shelso | |
| 6,471,718 B1 | 10/2002 | Staehle | |
| 6,640,412 B2 | 11/2003 | Iancea | |
| 6,689,123 B2 | 2/2004 | Pinchasik | |
| 6,823,576 B2 | 11/2004 | Austin | |
| 6,859,986 B2 | 3/2005 | Jackson | |
| 6,915,560 B2 | 7/2005 | Austin | |
| 7,402,171 B2 | 7/2008 | Osborne | |
| 8,100,959 B2 * | 1/2012 | Que et al. | 623/1.12 |

(Continued)

FOREIGN PATENT DOCUMENTS

| | | |
|---|---|---|
| DE | 19851846 | 5/2000 |
| EP | 0657147 | 6/1995 |

(Continued)

OTHER PUBLICATIONS

The International Bureau of WIPO, International Preliminary Report on Patentability, Jun. 17, 2010, for International Application No. PCT/US2008/085510.

(Continued)

*Primary Examiner* — Tuan V Nguyen
(74) *Attorney, Agent, or Firm* — Buchanan Nipper

(57) ABSTRACT

Storage and loading systems for expandable intraluminal medical devices are described. The systems include a container that defines an opening that tapers from a relatively large first diameter to a relatively small second diameter. A neck region includes structure adapted to engage an outer sheath of a delivery system such that an intraluminal medical device within the chamber of the container can be advanced through the tapered opening to effect compression of the intraluminal medical device and, ultimately, loading of the device into the delivery system. Methods of preparing and intraluminal medical device for implantation in a patient and kits useful in such methods are also described.

20 Claims, 8 Drawing Sheets

(56) References Cited

U.S. PATENT DOCUMENTS

| | | |
|---|---|---|
| 2002/0177899 A1 | 11/2002 | Eum |
| 2003/0055492 A1 | 3/2003 | Shaolian |
| 2003/0083730 A1 | 5/2003 | Stinson |
| 2003/0208254 A1 | 11/2003 | Shortt |
| 2003/0225445 A1 | 12/2003 | Derus |
| 2006/0064152 A1 | 3/2006 | Olson |
| 2006/0230592 A1 | 10/2006 | Heaney |
| 2007/0056346 A1 | 3/2007 | Spenser |
| 2007/0061009 A1 | 3/2007 | Spenser |
| 2007/0270931 A1 | 11/2007 | Leanna |
| 2007/0270932 A1 | 11/2007 | Headley |
| 2007/0270937 A1 | 11/2007 | Leanna |

FOREIGN PATENT DOCUMENTS

| | | |
|---|---|---|
| EP | 0938880 | 9/1999 |
| EP | 1362563 | 11/2003 |
| WO | 9959503 | 11/1999 |
| WO | 0040176 | 7/2000 |
| WO | 0249541 | 6/2002 |
| WO | 2007061801 | 5/2007 |

OTHER PUBLICATIONS

The International Searching Authority, International Search Report and the Written Opinion, Mar. 26, 2009, for International Application No. PCT/US2008/085510.

The International Searching Authority, International Search Report and the Written Opinion, Jul. 1, 2009, for International Application No. PCT/US2009/040026.

The International Bureau of WIPO, International Preliminary Report on Patentability, Jun. 17, 2010, for International Application No. PCT/US2008/085495.

The International Searching Authority, International Search Report and the Written Opinion, Apr. 2, 2009, for International Application No. PCT/US2008/085495.

* cited by examiner

STORAGE AND LOADING SYSTEM FOR IMPLANTABLE MEDICAL DEVICES

CROSS REFERENCE TO RELATED APPLICATION

This application claims priority to U.S. Provisional Application Ser. No. 61/005,351, filed on Dec. 4, 2007. The entire contents of this provisional application are hereby incorporated by reference into this disclosure.

FIELD

The disclosure relates generally to the field of implantable medical devices. More particularly, the invention relates to a system for storing and loading of an implantable medical device. Specific embodiments disclosed herein relate to storage and loading systems for percutaneously delivered intraluminal medical devices that include a tissue or other section of material in need of storage under hydrating conditions or in a hydrated state, such as certain stent graft and heart and venous valve devices.

BACKGROUND

Implantable medical devices that are delivered to a point of treatment using a delivery system must be loaded into the delivery system at some point prior to the implantation procedure. For some devices, this loading step can occur during the manufacturing process without adversely affecting the performance of the device. For example, expandable stents are typically loaded into their delivery system during the manufacturing process. When performing the implantation procedure, the clinician need not load the implantable medical device into the delivery system. Rather, the delivery system is simply removed from its packaging and put into use.

For some implantable medical devices, however, various concerns exist about the potential effects of extended storage within a delivery system. For example, it is well known that some medical device materials, such as tissues and biological-derived products, perform better when stored under hydrating conditions or in a hydrated state. Also, the long-term memory effects of reduced-diameter storage on some materials is not yet well understood, making it undesirable to store some devices in a delivery system prior to use.

For these implantable medical devices, it is sometimes necessary to store the device in a temporary storage vessel and instruct clinical personnel to load the device into an appropriate delivery system prior to the implantation procedure. Such storage and loading can even be used for those devices in which storage in a delivery system is not particularly undesirable. For example, storing stents separately from delivery systems may make it easier for clinicians to assemble device/delivery system combinations tailored to a particular patient and/or clinical presentation. For all instances in which a clinician must load the implantable device into a delivery system prior to implantation, it is desirable to make such loading procedures as simple and repeatable as possible.

Thus, a need exists for temporary storage and loading systems for implantable medical devices, methods of preparing an implantable medical device for implantation in a patient, and kits useful for the storage and loading of implantable medical devices.

SUMMARY OF EXEMPLARY EMBODIMENTS

Storage and loading systems, methods of preparing an implantable medical device for implantation in a patient, and kits useful for the storage and loading of implantable medical devices are described.

A storage and loading system according to an exemplary embodiment of the invention includes a container defining an interior chamber and a neck having an inner diameter, the interior chamber including a funnel that transitions from a relatively large first diameter to a relatively small second diameter that approximates the inner diameter of the neck; a delivery system having a sheath, a device holding chamber, and a grasper having a distal end with a grasping mechanism adapted to engage the implantable medical device, the sheath adapted to engage the neck of the container such that the implantable medical device can be moved from the interior chamber to the device holding chamber by retracting the distal end of the grasper from the chamber while the grasping mechanism is engaged with the implantable medical device.

A storage and loading system according to another exemplary embodiment comprises a container defining an interior chamber and a neck having an inner diameter, the container having a tapered inner surface that defines a funnel that transitions from a relatively large first diameter to a relatively small second diameter that approximates the inner diameter of the neck, the neck adapted to provide communication between the interior chamber and an external environment and having an inner surface defining a circumferential shoulder; an expandable intraluminal medical device disposed within the interior chamber, the intraluminal medical device including a support frame having first and second ends and a section of material capable of being hydrated attached to the support frame, the support frame defining an opening on an the first end of the support frame; a hydrating fluid disposed within the interior chamber and surrounding the expandable intraluminal medical device so as to place the section of material in a hydrated state; and a delivery system having a sheath with a terminal edge and a dilator defining a lumen, a device holding chamber cooperatively defined by the dilator and the sheath, and a grasper disposed through the lumen and having a distal end with a grasping mechanism adapted to engage the implantable medical device at the opening of the support frame, the sheath adapted to engage the neck of the container through an abutting relationship between the terminal edge and the shoulder of the inner surface of the neck such that the implantable medical device can be moved from the interior chamber to the device holding chamber by advancement of the grasper.

A storage and loading system according to another exemplary embodiment comprises a container defining an interior chamber and a neck having an inner diameter, the container having a tapered inner surface that defines a funnel that transitions from a relatively large first diameter to a relatively small second diameter that approximates the inner diameter of the neck, the neck adapted to provide communication between the interior chamber and an external environment and having an inner surface defining a circumferential shoulder and an outer surface defining a first thread; an expandable intraluminal medical device disposed within the interior chamber, the intraluminal medical device including a support frame having first and second ends and a section of material capable of being hydrated attached to the support frame, the support frame defining an opening on an the first end of the support frame; a hydrating fluid disposed within the interior chamber and surrounding the expandable intraluminal medical device so as to place the section of material in a hydrated state; a cap defining a second thread adapted to mate with the first thread; a disruptable seal disposed within the neck and adapted to prevent the hydrating fluid from escaping the interior chamber; and a delivery system having a sheath with a terminal edge and a dilator defining a lumen, a device holding chamber cooperatively defined by the dilator and the sheath, and a grasper disposed through the lumen and having a distal end with a grasping mechanism adapted to engage the implantable medical device at the opening of the support frame, the sheath adapted to engage the neck of the container through an abutting relationship between the terminal edge and the shoulder of the inner surface of the neck such that the implantable medical device can be moved from the interior chamber to the device holding chamber by advancement of the grasper.

A storage and loading system according to another exemplary embodiment comprises a container defining an interior chamber and a neck having an inner diameter, the container having a tapered inner surface that extends away from a longitudinal axis of the container at an internal angle that is between about 10 and about 12 degrees to define a funnel that transitions from a relatively large first diameter to a relatively small second diameter that approximates the inner diameter of the neck, the neck adapted to provide communication between the interior chamber and an external environment and having an inner surface defining a circumferential shoulder and an outer surface defining a first thread; an expandable intraluminal medical device disposed within the interior chamber, the intraluminal medical device including a support frame having first and second ends and a section of material capable of being hydrated attached to the support frame, the support frame defining an opening on an the first end of the support frame; a hydrating fluid disposed within the interior chamber and surrounding the expandable intraluminal medical device so as to place the section of material in a hydrated state; a cap defining a second thread adapted to mate with the first thread; a disruptable seal disposed within the neck and circumferentially attached to the inner surface of the neck, the disruptable seal adapted to prevent the hydrating fluid from escaping the interior chamber; and a delivery system having a sheath with a terminal edge and a dilator defining a lumen, a device holding chamber cooperatively defined by the dilator and the sheath, and a grasper disposed through the lumen and having a distal end with a grasping mechanism adapted to engage the implantable medical device at the opening of the support frame, the sheath adapted to engage the neck of the container through an abutting relationship between the terminal edge and the shoulder of the inner surface of the neck such that the implantable medical device can be moved from the interior chamber to the device holding chamber by retraction of the grasper.

Methods of preparing an intraluminal medical device for implantation in a patient are also described. A method according to an exemplary embodiment comprises the steps of comprising the steps of providing a storage and loading system according to an embodiment of the invention; engaging the delivery system with the storage and loading system; and advancing the implantable medical device from the storage and loading system and into a device holding chamber of the delivery system.

Kits are also described. A kit according to an exemplary embodiment of the invention includes a container containing a storage and loading system according to an embodiment of the invention, a delivery system, a grasper, and instructions for using the kit and/or the implantable medical device.

Additional understanding can be obtained with review of the detailed description of exemplary embodiments, appearing below, and the appended drawings illustrating exemplary embodiments.

DETAILED DESCRIPTION OF EXEMPLARY EMBODIMENTS

Figure 1:
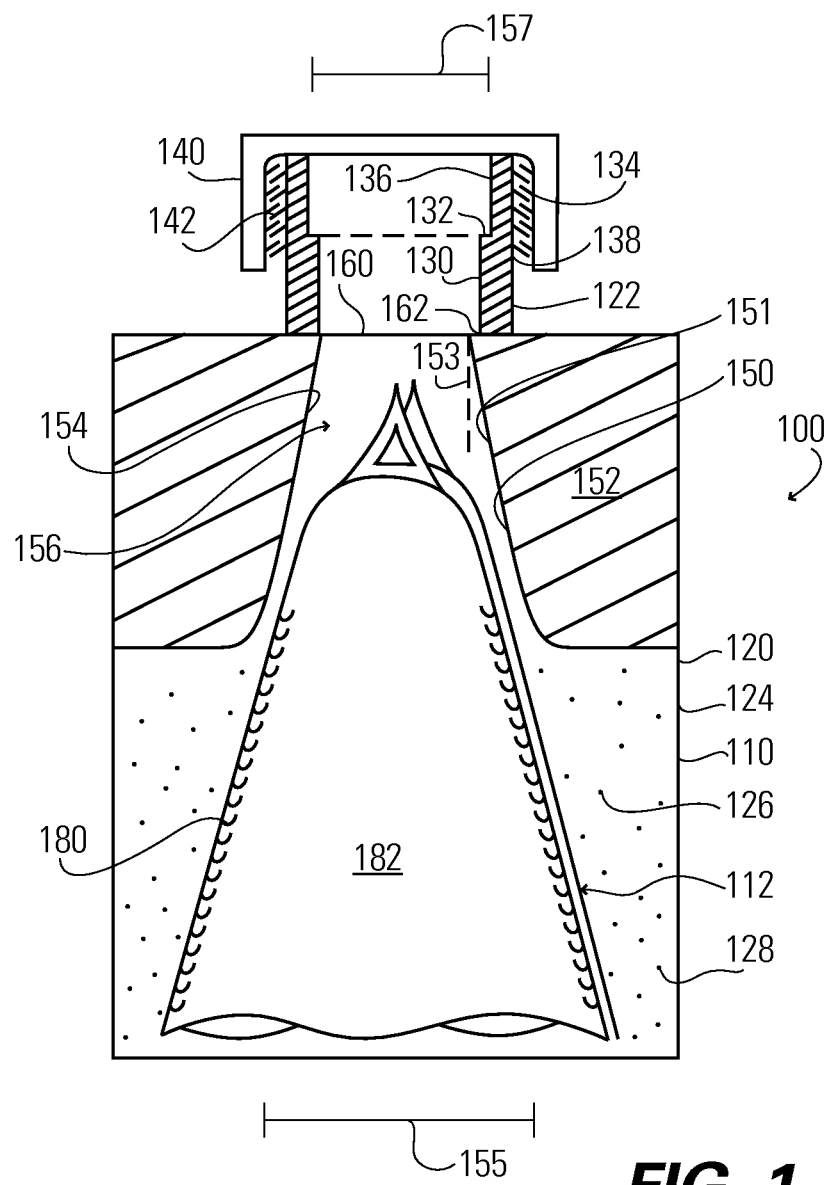
FIG. 1 is a sectional view of a storage and loading system according to a first exemplary embodiment.

The following detailed description and the appended drawings describe and illustrate various exemplary embodiments of the invention. The description and drawings are exemplary in nature and are provided to enable one skilled in the art to make and use one or more embodiments of the invention. They are not intended to limit the scope of the invention, or its protection, in any manner.

FIGS. 1, 2, 2A, and 3 illustrate a storage and loading system 100 according to a first exemplary embodiment. The system 100 includes a container 110 and an implantable medical device 112 disposed within the container 100.

The container 110 includes a main body 120 and a neck 122 or neck portion. The main body 120 includes a wall 124 that defines an interior chamber 126 of sufficient size to contain the implantable medical device 112. In this embodiment, the chamber 126 contains a fluid 128 in which the implantable medical device 112 is disposed. The fluid 128 can be any fluid, including suitable liquids and gases, suitable for extended storage of the implantable medical device 112. As such, a skilled artisan will be able to select an appropriate fluid for use in a particular storage and loading system according to a specific embodiment of the invention. As described below, the implantable medical device 112 in this embodiment is an intraluminal valve that includes a tissue component. The inventors have determined that phosphate buffered saline (PBS) and other saline solutions are appropriate fluids for use in storage and loading systems intended for use with such implantable medical devices.

The container 110 can be formed of any suitable material, and a skilled artisan will be able to select an appropriate material for use in a particular storage and loading system according to a specific embodiment of the invention based on various considerations, such as the desired weight and ruggedness of the container. The ability of the material to be subjected to particular sterilization processes may also be considered when selecting an appropriate material. The use of plastic containers is considered particularly advantageous at least because of their relatively light weight, ease of manufacturing, and acceptance in the medical device industry.

The neck 122 provides means for engaging a medical device delivery system 190 (illustrated in FIGS. 2, 2A, and 3, and detailed below) in a manner that allows the transfer of the intraluminal medical device 112 from the chamber 126 to the delivery system 190. In this embodiment, the neck 122 defines an upstanding wall member 130 that defines a shoulder 132 on its inner surface 136 and a thread 134 on its outer surface 138. The shoulder 132 advantageously extends around the entire inner circumference of the neck 122 as this is believed to provide a more stable engagement with a delivery system, as described below. It is noted, though, that one or more shoulders that extend around only a portion of the inner circumference of the neck 122 can be used. As best illustrated in FIG. 2A, a terminal edge of an outer sheath of the delivery system 190 rests on the shoulder 132 when the delivery system 190 and storage and loading system 110 are engaged.

A cap 140 includes a thread 142 that mates with thread 134 of the neck 122. When the cap 140 engages the neck 122 by formation of a threaded connection between threads 134, 142, the container 110 of the storage and loading system is closed to the external environment, thereby protecting the implantable medical device 112 therefrom. It is noted that, if the implantable medical device 112 is sterilized or is intended to be sterilized in the container 110, the threaded connection is advantageously one capable of maintaining a sterile environment within the chamber 126. That is, the threaded connection is advantageously able to prevent contaminants and/or potential contaminants from entering the chamber 126. Also advantageously, the threaded connection is able to prevent fluid 128 from escaping the chamber 126. It is considered advantageous that the threaded connection be one that is able to form and maintain a suitable hermetic seal in such embodiments, although this is considered optional. It is also noted that while mating threads 134, 142 are illustrated in connection with this embodiment, any suitable alternative structure can be used, such as a clamping mechanism. Indeed, any suitable means for forming a connection between a container neck and a container cap can be used and the illustrated structure simply provides an example.

Adjacent the neck 122, the container 110 includes a funnel 150 comprising a block 152 that having a tapered surface 154 that defines an opening 156. Because of its formation by the tapered surface 154, the opening has a relatively larger first diameter 155 at the end of the block 152 that is positioned opposite the neck 122 and a relatively smaller second 157 diameter at the end of the block 152 that is adjacent the neck 122. As best illustrated in FIG. 1, the second diameter 157 approximates the diameter of the opening of the neck 122.

The block 152 can be integrally formed with the container 110 or can comprise a separate member placed within the chamber 126. Furthermore, the block 152 can be formed from any suitable material, and need only allow the medical device to move along the tapered surface 154 during a loading procedure as described herein. Examples of suitable materials include plastics and other polymeric materials. A skilled artisan will be able to determine a suitable material for the block 152 without undue experimentation based on the nature of the medical device, the material of the container 110, and/or other considerations.

The relative sizes of the first 155 and second 157 diameters gives the opening 156 a frustoconical configuration, which provides a gradually shrinking diameter that, as described below, facilitates placement of the implantable medical device within a delivery system that is engaged with the neck 122 of the system 100. The taper of the tapered surface 154 is defined by an angle 151 between the surface 154 and an imaginary line 153 that extends parallel to or substantially parallel to a lengthwise axis of the container 110. To facilitate a smooth transition from the chamber 126 into an engaged delivery system 190, the angle 151 is advantageously a shallow angle. The inventors have determined that and angle of less than 45 degrees is particularly advantageous form several types of expandable intraluminal medical devices. The inventors have also determined that an angle of less than 20 degrees is particularly advantageous for expandable intraluminal medical devices that include a section of material attached to a support frame, such as a graft member attached to a support frame as in the illustrated prosthetic valve. Also, the inventors have determined that an angle of between about 10 degrees and about 12 degrees is considered particularly advantageous for medical devices that include a section of material attached to a support frame with attachment mechanisms, such as sutures or other suitable attachment mechanisms, along an outer edge of the support frame. Such an angle provides the desired tapered surface while minimizing and/or eliminating abrupt transitions in an expanded diameter of the medical device that could damage the connection between the material and the support frame. A skilled artisan will be able to determine a suitable angle for a storage and loading system according to a particular embodiment without undue experimentation based on various considerations, including the nature of the expandable intraluminal medical device and the desired overall size of the container.

As best illustrated in FIG. 1, the storage and loading system 100 is advantageously configured such that the interior chamber 126 has a length that extends from the inside bottom surface of the interior chamber 126 to the lower surface of the block 152 (i.e., the surface of the bloc 152 that is opposite the neck 122) and that is less than a length of the medical device 112 as measured along a lengthwise axis thereof. This configuration ensures that a portion of the medical device 112 is positioned within the opening 156 when stored in the interior chamber 126, which is expected to stabilize the medical device during storage, handling and transport. Any suitable relative lengths of the interior chamber 126 and the medical device 112 can be used, and a skilled artisan can determine appropriate relative lengths for a storage and loading system according to a particular embodiment based on various considerations, including the nature of the medical device 112, the nature of the hydrating fluid 128, the extend of expected handling during storage, etc. A chamber length that is <99% of the length of the implantable medical device 112 is believed to be acceptable. A chamber length that is <95% of the length of the implantable medical device 112 is considered more advantageous. A chamber length that is <90% of the length of the implantable medical device 112 is considered more advantageous. A chamber length that is <75% of the length of the implantable medical device 112 is considered suitable. A chamber length that is <50% of the length of the implantable medical device 112 may be suitable and desirable for certain types of medical devices for which very little to no movement within the chamber 126 is desired. No matter the length selected, the tapered surface 154 of the funnel 150 is advantageously simply extended along the same plane and at the same angle relative to the lengthwise axis of the container 110.

The storage and loading system 100 according to this embodiment includes a disruptable seal 160 that regulates the passage of the implantable medical device 112 from the chamber 126 into the neck 122. While inclusion of the disruptable seal 160 is considered optional, its inclusion in the system 100 is considered to be advantageous at least because it provides a mechanical barrier between the chamber 126 and neck 122 that can prevent the implantable medical device 112 from becoming lodged in the neck 122 prior to a loading procedure, such as during storage and transport. Furthermore, the disruptable seal 160 provides an additional barrier to the entry of potential contaminants into the chamber 126. Any suitable mechanical seal can be used for the disruptable seal 160. In the illustrated embodiment, the disruptable seal 160 comprises a piece of foil disposed at and circumferentially attached to the neck 122 with adhesive 162. Other suitable structures include polymeric material attached in similar or different fashion and a removable compressible or rigid plug disposed within the neck 122.

It is noted that the implantable medical device 112 can be any suitable implantable medical device that would benefit from the features and/or advantages provided by a storage and loading system according to an embodiment of the invention. Generally, implantable medical devices that require or would benefit from storage in an expanded or partially expanded configuration and/or storage in a particular fluid, such as a particular liquid or gas, can be used in storage and loading systems according to the invention. Exemplary implantable medical devices suitable for use in storage and loading systems according to embodiments of the invention include those having one or more components made from a material or materials expected or believed to perform better when stored under hydrating conditions or in a hydrated state, such as tissue and other biological-derived materials. Also, storage and loading systems according to the invention are particularly well-suited for use with intraluminal medical devices that include a self-expandable support frame, including frames made of nitinol, stainless steel, and other resilient materials.

Figure 2:
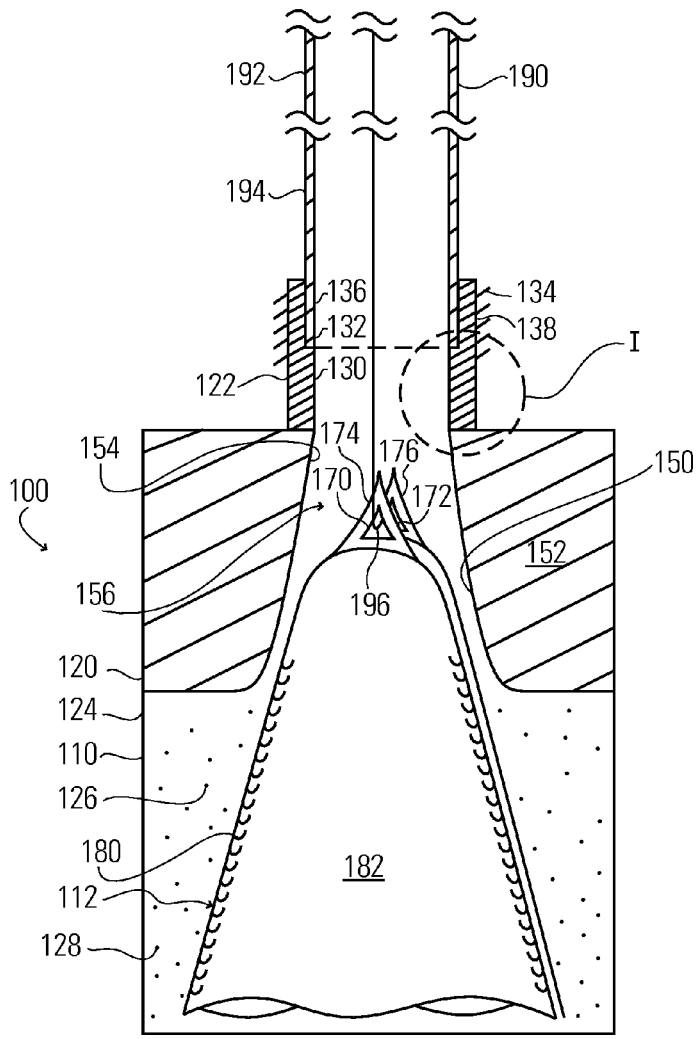
FIG. 2 is a sectional view of the storage and loading system illustrated in FIG. 1 engaged with a delivery system into which loading of the intraluminal medical device can occur.
Figure 2A:
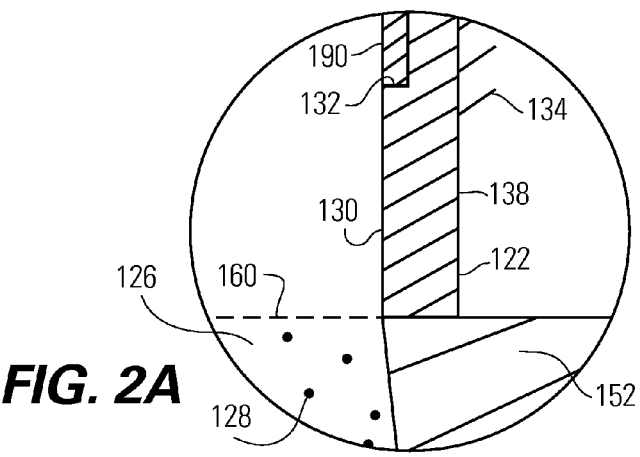
FIG. 2A is a magnified view of Area I highlighted in FIG. 2.
Figures 3, 3A:
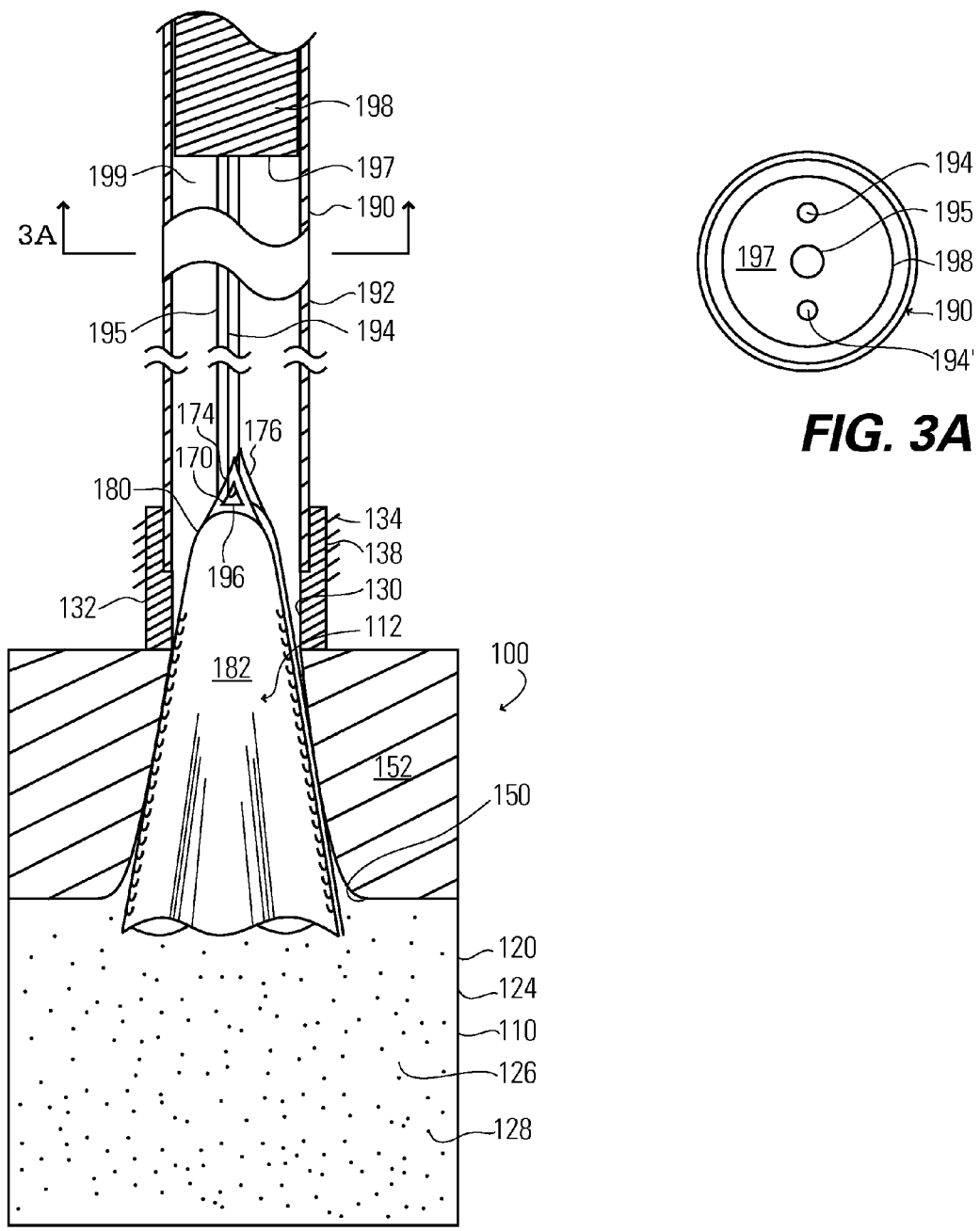
FIG. 3 is a partial sectional view of the storage and loading system and the engaged delivery system illustrated in FIG. 2. The intraluminal medical device is shown in the midst of being loaded into the delivery system.
FIG. 3A is a cross section view of the delivery system illustrated in FIG. 3, taken along line 3A-3A.

The embodiment illustrated in FIGS. 1, 2, 2A, and 3 includes an implantable medical device 112 that comprises an implantable venous valve. The device 112 includes a support frame 180 and an attached leaflet 182 formed from fixed tissue, such as fixed tissue excised from an animal valve. The valve device 112 can comprise any suitable implantable valve device, and need only include suitable structure that enables the device to be engaged by a hook or other suitable engaging means, as described in detail below. In the embodiment illustrated in FIGS. 1, 2, and 3, the support frame 180 of the valve device 112 includes openings 170, 172 formed on the ends 174, 176 of the support frame 180. As best illustrated in FIGS. 2 and 3, the openings 170, 172 expose an edge of the support frame 180 that can be engaged by a hook or other suitable means for engaging the support frame 180 to effect retraction of the valve device 112 from the chamber 126.

Examples of suitable valve devices that could be modified to include aspects of the invention and to work as in or as part of a disclosed storage and loading system can be found U.S. Pat. No. 7,402,171 to Osborne, et. al for a PROSTHETIC VALVE THAT PERMITS RETROGRADE FLOW and U.S. patent application Ser. No. 12/252,918 filed on Oct. 16, 2008, by Chambers, et. al for an IMPLANTABLE VALVE DEVICE, each of which is expressly incorporated by reference into this disclosure for the purpose of describing suitable implantable medical devices that can be modified in accordance with the inventive concepts disclosed herein.

The openings 170, 172 can have any suitable size, shape, configuration, and number, and the parameters chosen for a storage and loading system according to a particular embodiment of the invention will depend on various factors, including the nature of the device and support frame and the desired overall size of the device and frame. The device 112 illustrated in FIGS. 1, 2, and 3 includes a pair of openings 170, 172, each of which is defined by a closed edge of the support frame 180. The openings 170, 172 are integrally formed in a barb structure on the ends 174, 176 of the support frame 180. This configuration is believed to be advantageous at least because it provides barb and loading functions without adding significant bulk to the valve device.

Figure 3B:
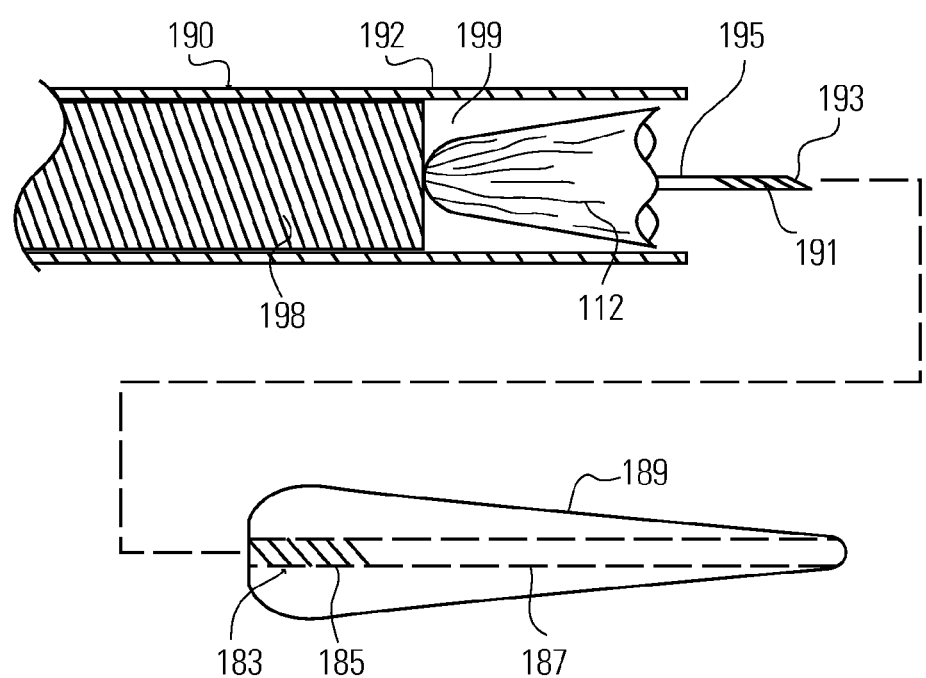
FIG. 3B is an exploded view of a fully assembled delivery system following loading of the intraluminal medical device.

FIGS. 3, 3A, and 3B illustrates a loading process. FIG. 3A illustrates the storage and loading system 100 and an engaged delivery system 190. The intraluminal medical device 112 is shown in the midst of being loaded into the delivery system 190. The delivery system 190 includes an outer sheath 192 and an elongate grasper 194 disposed within the sheath 190. The distal end of the grasper 194 provides a hook 196 for engaging one of the openings 170, 172 of the valve device 112. A dilator 198 is disposed within the sheath and has a blunt distal end 197 that cooperatively forms a device holding chamber 199 with the sheath 190. The implantable intraluminal medical device 112 is placed within the device holding chamber during a loading process. The grasper 194 is a wire member disposed through a lumen formed by the dilator 198. The dilator 198 also includes an extension tube 195 that defines a wireguide lumen 193 and includes a threaded end 191. As best illustrated in FIG. 3A, a second grasper 194' can also be provided.

In FIG. 3, the delivery system 190 is engaged with the storage and loading system 100. The cap (not illustrated) has been removed from the neck 122, and the sheath 192 has been inserted into the interior of the neck 122 until the distal end of the sheath abuts the shoulder 132 formed by the wall 130. As illustrated in FIG. 3, loading of the implantable medical device 112 into the delivery system 190 has been initiated. The grasper 194 has been extended out of the distal end of the delivery system 190 and into the chamber 122 of the container 110. The hook 196 has engaged the edge of the support frame at the opening 170, and the clinician has begun to pull the distal end of the grasper 194 out of the chamber 122 and back into the sheath 192. Because of the engagement between the hook 196 and the implantable medical device 112, the device 112 moves with this movement of the grasper 194, passing over the extension tube 195 in the process. The medical device 112 has begun to compress via interaction with the tapered surface 154 provided by the funnel 150. To complete the loading procedure, the clinician need only continue retracting the grasper 194 until the medical device 112 is placed within the holding chamber 199 in its radially compressed configuration. The engagement is then broken by advancing the hook 196 in an opposite direction until it exits the opening 170. The distal ends of the grasper 194 can be configured to have an outwardly directed bias to facilitate this disengagement. Once disengagement of the medical device 112 is achieved, the clinician can disengage the delivery system 190 from the storage and loading system 100, such as by retracting the sheath 192 from the neck 122 of the container 110.

As illustrated in FIG. 3B, a dilator tip 189 that defines a wireguide lumen 187 with a thread 185 along a proximal portion 183 thereof can then be attached to the extension tube 195 to form the complete loaded delivery system. At this time, the delivery system is ready for use according to conventional percutaneous techniques.

Figure 4:
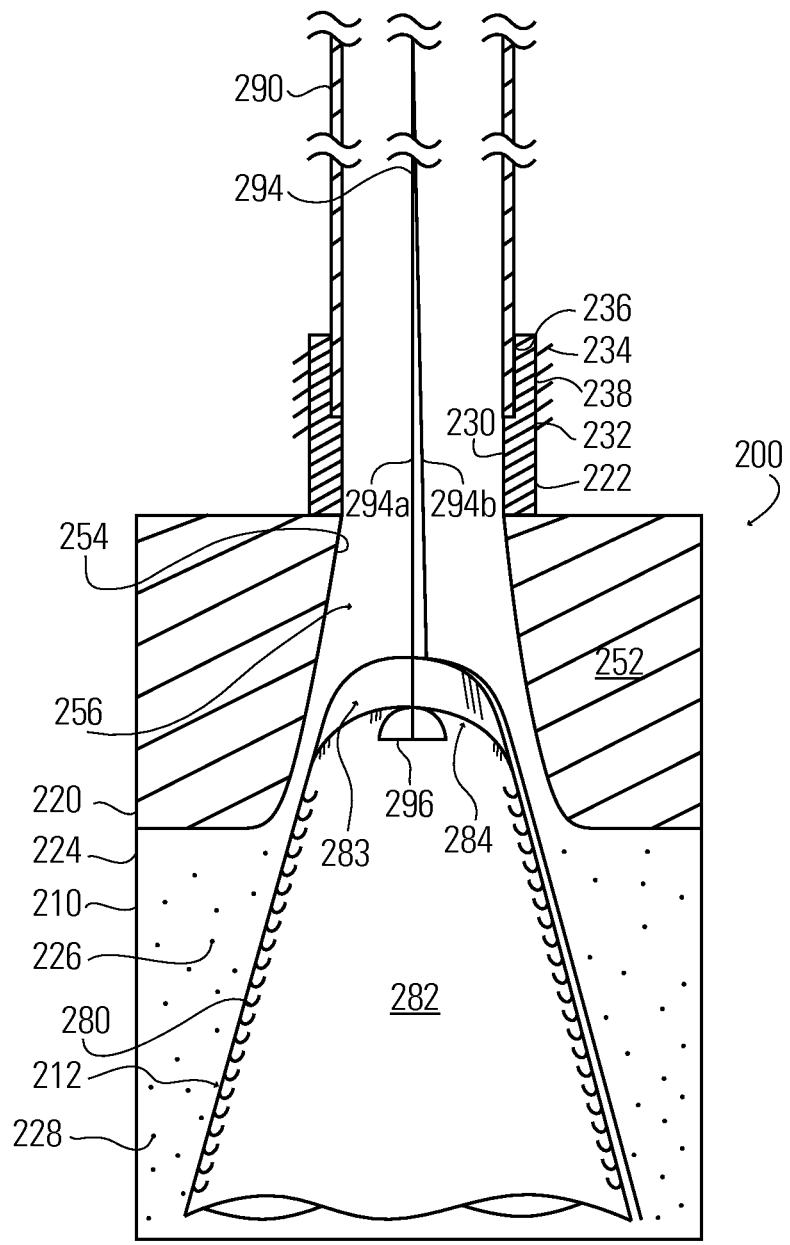
FIG. 4 is a sectional view of a storage and loading system according to an alternative embodiment.

FIG. 4 illustrates a storage and loading system 200 according to another alternative embodiment. The storage and delivery system according to this embodiment is similar to the other embodiments described herein, except as detailed below. Accordingly, the system 200 includes a container 210 in which an implantable medical device 212 can be disposed. The container 210 includes a main body 220 and a neck 222. The main body 220 includes a wall 224 that defines an interior chamber 226 of sufficient size to contain the implantable medical device 212. The chamber 226 contains a fluid 228 in which the implantable medical device 212 is disposed. The neck 222 provides means for engaging a medical device delivery system as described above. The neck 222 defines an upstanding wall member 230 that defines a shoulder 232 on its inner surface 236 and a thread 234 on its outer surface 238. A cap (not illustrated in FIG. 4) includes a thread that mates with thread 234 of the neck 222. The container 210 includes a funnel 250 comprising a block 252 having a tapered surface 254 that defines an opening 256. The opening 256 has a relatively larger first diameter at the end of the block 252 that is positioned opposite the neck 222 and a relatively smaller second diameter at the end of the block 252 that is adjacent the neck 222.

In this embodiment, the leaflet 284 of the implantable medical device 212 includes a section 283 that forms an outwardly facing pocket 284. The delivery system 290 includes a grasper 294 having a grasping mechanism that comprises a hook 296 that substantially conforms to the shape of the pocket 284. Thus, the hook 296 in this embodiment is adapted to engage the implantable medical device 212 by way of snagging the section 283 of the leaflet 284. The section 283, pocket 284, and hook 296 can comprise any suitable size, type, and configuration, and a skilled artisan can determine appropriate configurations for use in a storage and loading system according to a particular embodiment of the invention based on various considerations, including the nature of the leaflet 284 and the intended use of the medical device 212. A section 283 that comprises a fixed section of the leaflet 284 is considered particularly advantageous at least because it is expected to enable the section 283 to withstand the pulling forces exerted thereon by the hook 296 during a loading procedure.

Also in this embodiment, the grasper 294 includes two terminal portions 294a, 294b that each include a hook 296 (only one is illustrated in FIG. 4). While the use of multiple hooks or other grasping mechanisms is considered optional, it may be advantageous at least because it is expected to minimize or eliminate skewing of the medical device during retraction and loading. Any number of suitable grasping mechanisms can be used, including any number of hooks, and a skilled artisan will be able to determine a suitable number based on various considerations, including the nature of the medical device and the desired bulk of the grasper and delivery system. For the bileaflet valve devices illustrated herein, the inventors have determined that a grasper 294 that includes two grasping mechanisms 296 is suitable.

A clinician uses this system 200 similar to the system described above: by advancing the grasping mechanism 296 into the chamber 226 and engaging the medical device 312 by working the hook 296 into the pocket 284 to snag the section 283 of the leaflet 282. Once an engagement is made, the grasper 294 is retracted into the sheath of the delivery system 290, forcing the medical device 212 through the funnel 250 and thereby into a compressed configuration and ultimately into the device holding chamber of the delivery system 290. The engagement is then broken by advancing the hook 296 in an opposite direction until it exits the pocket 284. If a grasper 294 having dual hooks, such as the grasper illustrated in FIG. 4, is used, engagements with two sections 283 of the medical device 212 are advantageously made.

Figure 5:
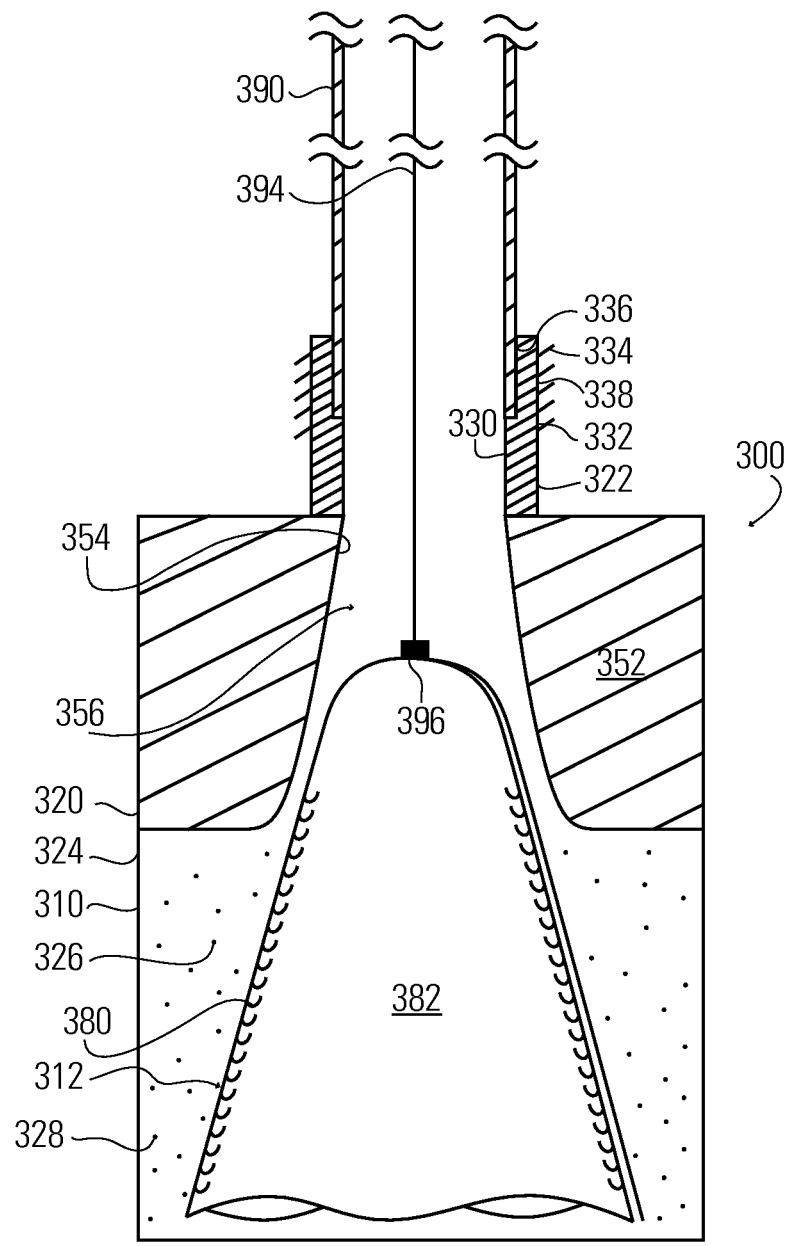
FIG. 5 is a sectional view of a storage and loading system according to another alternative embodiment.

FIG. 5 illustrates a storage and loading system 300 according to another alternative embodiment. The storage and delivery system according to this embodiment is similar to the other embodiments described herein, except as detailed below. Accordingly, the system 300 includes a container 310 in which an implantable medical device 312 can be disposed. The container 310 includes a main body 320 and a neck 322. The main body 320 includes a wall 324 that defines an interior chamber 326 of sufficient size to contain the implantable medical device 312. The chamber 326 contains a fluid 328 in which the implantable medical device 312 is disposed. The neck 322 provides means for engaging a medical device delivery system as described above. The neck 322 defines an upstanding wall member 330 that defines a shoulder 332 on its inner surface 336 and a thread 334 on its outer surface 338. A cap (not illustrated in FIG. 5) includes a thread that mates with thread 334 of the neck 322. The container 310 includes a funnel 350 comprising a block 352 having a tapered surface 354 that defines an opening 356. The opening 356 has a relatively larger first diameter at the end of the block 352 that is positioned opposite the neck 322 and a relatively smaller second diameter at the end of the block 352 that is adjacent the neck 322.

In this embodiment, the delivery system includes a grasper 394 having a grasping mechanism that comprises a magnet 396 adapted to engage the implantable medical device by way of magnetic attraction to a metal support frame 380 of the implantable medical device 312. The magnet can comprise any suitable size, type, and configuration, and a skilled artisan can determine an appropriate magnet for use in a storage and loading system according to a particular embodiment of the invention based on various considerations, including the nature of the support frame. Rare earth magnets are considered particularly advantageous at least because of the relatively high magnetic strength in a relatively compact size.

A clinician using this system 300 similar to the system described above: by advancing the grasping mechanism 396 into the chamber 326 until the magnet 396 engages the medical device 312 (i.e., forms a magnetic attachment to the support frame or other portion of the device 312), and then retracting the grasper 394 into the sheath of the engaged delivery system, forcing the medical device 312 through the funnel 350 and thereby into a compressed configuration and ultimately into the device holding chamber of the delivery system. The magnetic connection is then broken using any suitable technique, including mechanical disruption of the connection.

Figure 6:
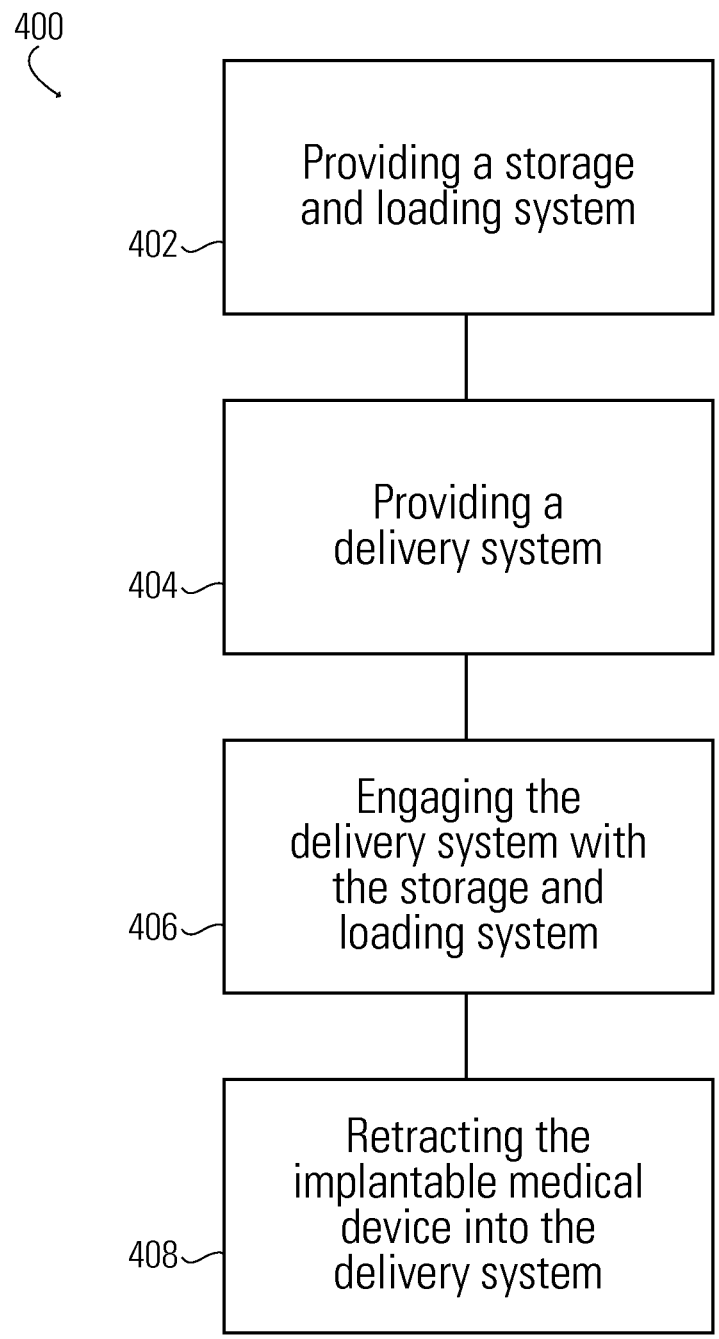
FIG. 6 is a flow chart illustrating an exemplary method of preparing an intraluminal medical device for implantation in a patient.

FIG. 6 illustrates an exemplary method 400 of preparing an implantable medical device for implantation in a patient. The method includes the step 402 of providing a storage and loading system according to the invention having an implantable medical device stored therein. Each of the embodiments described herein provides an example of a suitable storage and loading system for use in the inventive methods. Another step 404 comprises providing a delivery system capable of engaging the storage and delivery system in a manner that permits transfer of the implantable medical device from the storage and loading system to the delivery system. Another step 406 comprises engaging the delivery system with the storage and loading system. Another step 408 comprises advancing the implantable medical device from the storage and loading system and into a device holding chamber of the delivery system.

In one exemplary method, the step of engaging the delivery system with the storage and loading system comprises inserting a sheath of the delivery system into a neck of the storage and loading system.

In one exemplary method, the step of advancing the implantable medical device from the storage and loading system and into the device holding chamber of the delivery system comprises engaging the implantable medical device with a grasping mechanism. In one exemplary embodiment, the advancing is accomplished by retracting the implantable medical device into the device holding chamber. In another exemplary embodiment, the advancing is accomplished by pushing the implantable medical device into the device holding chamber. If pushing is employed, a storage and loading system with appropriate structureal modifications should be used. For example, a secondary opening, opposite the neck of the container, can be used to insert the grasper and engage the medical device prior to pushing the grasper and engaged medical device through the neck and into the engaged delivery system.

Figure 7:
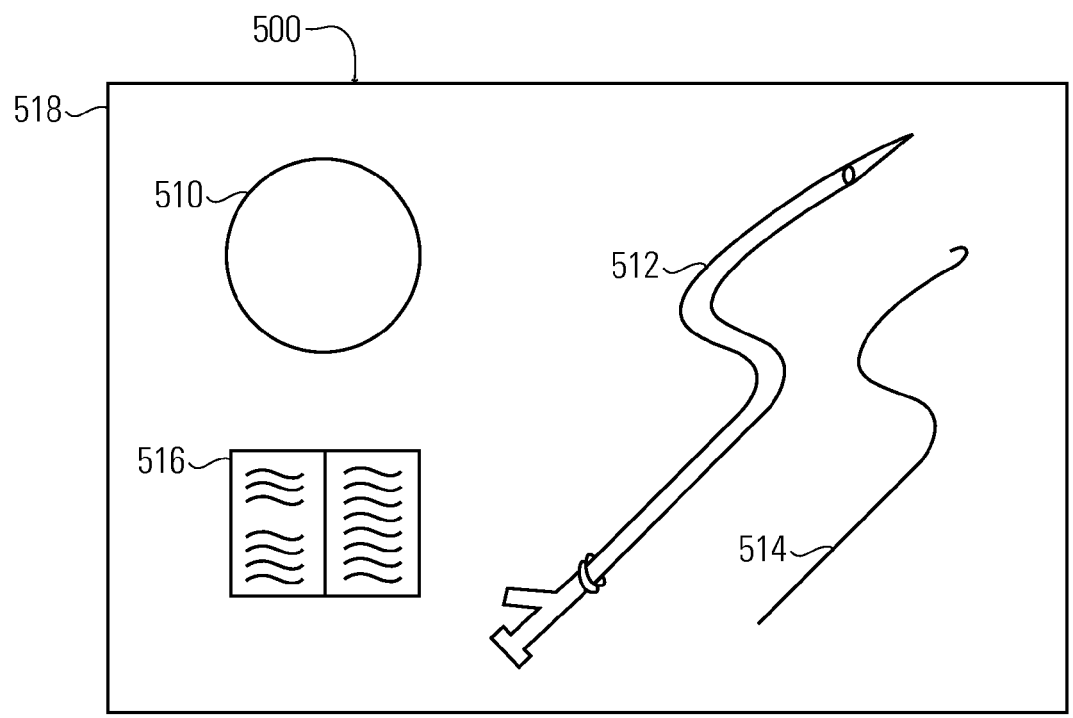
FIG. 7 is a schematic of a kit according to an exemplary embodiment of the invention.

FIG. 7 illustrates a kit 500 according to an exemplary embodiment. Kits according to embodiments of the invention are useful for the storage and loading of implantable medical devices. The kit 500 according to this embodiment includes a storage and loading system 510 according to an embodiment of the invention, a delivery system 512, a grasper 514, and optional instructions 516 for using the kit and/or its components. The storage and loading system 510 includes an implantable medical device stored therein, and the delivery system 512 is capable of engaging the storage and loading 510 system in a manner that permits transfer of the implantable medical device from the storage and loading system 510 to the delivery system 512, as described herein. The components of the kit 500 are advantageously included in a storage container 518, such as a cardboard or plastic box.

The foregoing detailed description provides exemplary embodiments of the invention and includes the best mode for practicing the invention. The description and illustration of embodiments is intended only to provide examples of the invention and not to limit the scope of the invention, or its protection, in any manner.

What is claimed is:

1. A storage and loading system for an implantable medical device, said system comprising:
   a container defining an interior chamber and a neck having an inner diameter, the container having a tapered inner surface that defines a funnel that transitions from a relatively large first diameter to a relatively small second diameter that approximates the inner diameter of the neck, the neck adapted to provide communication between the interior chamber and an external environment and having an inner surface defining a circumferential shoulder;
   an expandable intraluminal medical device disposed within the interior chamber, the intraluminal medical device including a support frame having first and second ends and a section of material capable of being hydrated attached to the support frame, the support frame defining an opening on an the first end of the support frame;
   a hydrating fluid disposed within the interior chamber and surrounding the expandable intraluminal medical device so as to place the section of material in a hydrated state; and
   a delivery system having a sheath with a terminal edge and a dilator defining a lumen, a device holding chamber cooperatively defined by the dilator and the sheath, and a grasper disposed through the lumen and having a distal end with a grasping mechanism adapted to engage the implantable medical device at the opening of the support frame, the sheath adapted to engage the neck of the container through an abutting relationship between the terminal edge and the circumferential shoulder of the inner surface of the neck such that the implantable medical device can be moved from the interior chamber to the device holding chamber by advancement of the grasper.

2. The storage and loading system according to claim 1, wherein the neck includes an external surface defining a first thread and further comprising a cap having a second thread adapted to mate with the first thread so as to provide a hermetic seal.

3. The storage and loading system according to claim 1, further comprising a disruptable seal disposed within the neck.

4. The storage and loading system according to claim 3, wherein the disruptable seal is circumferentially attached to the inner surface of the neck.

5. The storage and loading system according to claim 3, wherein the disruptable seal comprises a foil sheet.

6. The storage and loading system according to claim 1, wherein the tapered inner surface is integrally formed by the container.

7. The storage and loading system according to claim 1, wherein the tapered inner surface extends away from a longitudinal axis of the container at an internal angle that is less than about 45 degrees.

8. The storage and loading system according to claim 1, wherein the tapered inner surface extends away from a longitudinal axis of the container at an internal angle that is less than about 20 degrees.

9. The storage and loading system according to claim 1, wherein the tapered inner surface extends away from a longitudinal axis of the container at an internal angle that is between about 10 and about 12 degrees.

10. The storage and loading system according to claim 1, wherein the section of material of the expandable intraluminal medical device comprises a section of tissue.

11. The storage and loading system according to claim 1, wherein the expandable intraluminal medical device is a valve device adapted to regulate fluid flow through a body vessel of a patient.

12. A storage and loading system for an implantable medical device, said system comprising:
   a container defining an interior chamber and a neck having an inner diameter, the container having a tapered inner surface that defines a funnel that transitions from a relatively large first diameter to a relatively small second diameter that approximates the inner diameter of the neck, the neck adapted to provide communication between the interior chamber and an external environment and having an inner surface defining a circumferential shoulder and an outer surface defining a first thread;
   an expandable intraluminal medical device disposed within the interior chamber, the intraluminal medical device including a support frame having first and second ends and a section of material capable of being hydrated attached to the support frame, the support frame defining an opening on an the first end of the support frame;
   a hydrating fluid disposed within the interior chamber and surrounding the expandable intraluminal medical device so as to place the section of material in a hydrated state;
   a cap defining a second thread adapted to mate with the first thread;
   a disruptable seal disposed within the neck and adapted to prevent the hydrating fluid from escaping the interior chamber; and
   a delivery system having a sheath with a terminal edge and a dilator defining a lumen, a device holding chamber cooperatively defined by the dilator and the sheath, and a grasper disposed through the lumen and having a distal end with a grasping mechanism adapted to engage the implantable medical device at the opening of the support frame, the sheath adapted to engage the neck of the container through an abutting relationship between the terminal edge and the circumferential shoulder of the inner surface of the neck such that the implantable medical device can be moved from the interior chamber to the device holding chamber by advancement of the grasper.

13. The storage and loading system according to claim 12, wherein the disruptable seal is circumferentially attached to the inner surface of the neck.

14. The storage and loading system according to claim 12, wherein the disruptable seal comprises a foil sheet.

15. The storage and loading system according to claim 12, wherein the tapered inner surface extends away from a longitudinal axis of the container at an internal angle that is less than about 45 degrees.

16. The storage and loading system according to claim 12, wherein the tapered inner surface extends away from a longitudinal axis of the container at an internal angle that is less than about 20 degrees.

17. The storage and loading system according to claim 12, wherein the tapered inner surface extends away from a longitudinal axis of the container at an internal angle that is between about 10 and about 12 degrees.

18. The storage and loading system according to claim 12, wherein the section of material of the expandable intraluminal medical device comprises a section of tissue.

19. The storage and loading system according to claim 12, wherein the expandable intraluminal medical device is a valve device adapted to regulate fluid flow through a body vessel of a patient.

20. A storage and loading system for an implantable medical device, said system comprising:
a container defining an interior chamber and a neck having an inner diameter, the container having a tapered inner surface that extends away from a longitudinal axis of the container at an internal angle that is between about 10 and about 12 degrees to define a funnel that transitions from a relatively large first diameter to a relatively small second diameter that approximates the inner diameter of the neck, the neck adapted to provide communication between the interior chamber and an external environment and having an inner surface defining a circumferential shoulder and an outer surface defining a first thread;
an expandable intraluminal medical device disposed within the interior chamber, the intraluminal medical device including a support frame having first and second ends and a section of material capable of being hydrated attached to the support frame, the support frame defining an opening on an the first end of the support frame;
a hydrating fluid disposed within the interior chamber and surrounding the expandable intraluminal medical device so as to place the section of material in a hydrated state;
a cap defining a second thread adapted to mate with the first thread;
a disruptable seal disposed within the neck and circumferentially attached to the inner surface of the neck, the disruptable seal adapted to prevent the hydrating fluid from escaping the interior chamber; and
a delivery system having a sheath with a terminal edge and a dilator defining a lumen, a device holding chamber cooperatively defined by the dilator and the sheath, and a grasper disposed through the lumen and having a distal end with a grasping mechanism adapted to engage the implantable medical device at the opening of the support frame, the sheath adapted to engage the neck of the container through an abutting relationship between the terminal edge and the circumferential shoulder of the inner surface of the neck such that the implantable medical device can be moved from the interior chamber to the device holding chamber by advancement of the grasper.

* * * * *